United States Patent [19]
Waldmann et al.

[11] 3,972,944
[45] Aug. 3, 1976

[54] PROCESS FOR PREPARING ALDEHYDES FROM OLEFINS

[75] Inventors: Helmut Waldmann, Leverkusen; Wulf Schwerdtel, Leverkusen-Steinbuechel; Wolfgang Swodenk, Odenthal-Gloebusch, all of Germany

[73] Assignee: Bayer Aktiengesellschaft, Leverkusen, Germany

[22] Filed: Oct. 26, 1973

[21] Appl. No.: 410,075

[30] Foreign Application Priority Data
Oct. 27, 1972  Germany............................ 2252674

[52] U.S. Cl................................ 260/599; 260/598; 260/600 R; 260/601 H; 260/602; 260/604 R
[51] Int. Cl.²............ ........ C07C 47/52; C07C 47/54; C07C 47/12; C07C 47/28
[58] Field of Search................ 260/599, 604 R, 598, 260/600, 601 H, 602

[56] References Cited
UNITED STATES PATENTS

| | | | |
|---|---|---|---|
| 3,029,288 | 4/1962 | Etherington, Jr. .............. | 260/604 R |
| 3,057,915 | 10/1962 | Riemenschneider et al. ....... | 260/599 |
| 3,255,238 | 6/1966 | Roelen et al..................... | 260/604 R |

FOREIGN PATENTS OR APPLICATIONS

| | | | |
|---|---|---|---|
| 1,802,003 | 3/1971 | Germany..................... | 260/604 R X |

OTHER PUBLICATIONS

Roberts et al., *Organic Chemistry* pp. 190–191, 417, 1226–1227 (1964).

Primary Examiner—James O. Thomas, Jr.
Assistant Examiner—Nicky Chan
Attorney, Agent, or Firm—Burgess, Dinklage & Sprung

[57] ABSTRACT

Aldehydes are prepared by reacting an olefin with hydrogen peroxide in the presence of at least one boron compound and at least one compound of one of the metals of the fifth and/or sixth Secondary Group of the Periodic Table.

12 Claims, No Drawings

PROCESS FOR PREPARING ALDEHYDES FROM OLEFINS

BACKGROUND

This invention relates to a process for the production of aldehydes by reacting olefins with hydrogen peroxide.

Aldehydes are important intermediate products for the synthesis of medicaments or azo dyes. Certain aldehydes, for example glutardialdehydes, are used as tanning agents.

It is known that aldehydes can be obtained by a two-stage process in the first stage of which certain olefins are reacted with hydrogen peroxide to form the corresponding 1,2-diols which are subsequently converted in the second stage into the corresponding aldehydes by reaction with compounds such as lead tetra-acetate (R. Criegee, *Ber. d. dtsch. chem. Ges.* 64, 264 (1931)) or periodic acid (L. Malaprade, *Bull. Soc. Chim. France* (4) 43, 683 (1928)).

One disadvantage of this process is that the 1,2-diols have to be prepared as intermediate products. Another disadvantage is that the oxidising agents used in the second stage, such as lead tetra-acetate or periodic acid, do not have a catalytic effect upon the reaction, instead they actually take part in it. Thus, the conversion products of the oxidising agents used for splitting the 1,2-diols have to be isolated on completion of the reaction and converted into the corresponding oxidising starting compounds before they are reused.

SUMMARY

It has now been found that aldehydes can be directly obtained by reacting an olefin with hydrogen peroxide, providing the reaction is carried out in the presence of a compound of boron and a compound of a metal of the 5th and/or 6th Secondary Group.

DECRIPTION

Olefins suitable for use in the process according to the invention are compounds corresponding to the general formula (I)

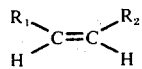

in which $R_1$ and $R_2$ independently of one another represent hydrogen, a phenyl group optionally substituted by fluorine, chlorine, cyanide, $C_1$-$C_6$-alkoxy or $C_1$-$C_6$-alkyl, a linear or branched $C_1$-$C_{12}$-alkyl radical optionally substituted by fluorine, chlorine, OH, $C_1$-$C_6$-alkoxy, carbo-$C_1$-$C_3$-alkoxy, cyanide or phenyl, in addition to which the radicals $R_1$ and $R_2$ together with the carbon atoms of the C=C-double bond can represent a carbocyclic ring with up to 24 carbon atoms optionally substituted by fluorine, chlorine, cyanide, $C_1$-$C_6$-alkyl, $C_5$-$C_6$-cycloalkyl or phenyl.

The following are examples of substituted phenyl groups: 4-chlorophenyl, 2,4-dichlorophenyl, 4-methoxyphenyl, 4-chloro-2-methoxyphenyl, 4-propoxyphenyl, 4-tert.-butoxyphenyl, 4-n-hexoxyphenyl, 4-cyanophenyl and 4-cyano-3,5-dimethylphenyl.

The following are mentioned as examples of linear or branched $C_1$-$C_{12}$-alkyl radicals: methyl, ethyl, propyl, n-butyl, isobutyl, tert.-butyl, pentyl, hexyl, heptyl, octyl, nonyl, decyl, undecyl, dodecyl, pentadecyl, hexadecyl, octadecyl and their isomers. $C_2$-$C_6$-alkyl radicals are preferably used.

The following are mentioned as specific examples of substituted alkyl radicals: chloromethyl, β-chloroethyl, 2-(β-ethyl)-hexyl, 2,4-diisopropyl, hydroxymethyl, β-hydroxyethyl, ω-hydroxyhexyl, 2-hydroxymethylhexyl, β-methoxyethyl, 3-propoxypropyl, n-hexoxymethylhexyl, 2,4,6-trimethoxyhexyl, 2-(methoxymethyl)-propyl, carbomethoxymethyl, 3-(carbopropoxy)-propyl, 3-(carbomethoxy)-hexyl, 3-(β-carbomethoxyethyl)-butyl, β-cyanoethyl, 2-(β-cyanoethyl)-propyl, ω-cyanoheptyl and ω-cyanooctyl.

The following are examples of phenyl groups substituted by a linear or branched alkyl radical with up to 6 C-atoms: tolyl, ethylphenyl, propylphenyl, n-butylphenyl, tert.-butylphenyl, di-tert.-butylphenyl, tri-tert.-butylphenyl. It is preferred to use phenyl groups substituted by a $C_1$-$C_3$-alkyl radical.

The following are examples of $C_1$-$C_{12}$-alkyl radicals substituted by a phenyl radical: phenylmethyl, phenylethyl, phenylpropyl, phenyl-tert.-butyl, ω-phenylhexyl. It is preferred to use $C_2$-$C_6$-alkyl radicals substituted by phenyl.

The following olefins are mentioned by way of example: ethylene, propylene, 1-butylene, 2-butylene, isobutylene, 1-pentene, 2-pentene, 1-hexene, 2-hexene, 3-hexene, 1-heptene, 2-heptene, 3-heptene, 1-octene, non, 1-decene, 2-decene, 1-undecene, 4-undecene, 5-decene, 2,5-dimethyl-3-hexene, 2,2,5,5-tetramethyl-3-hexene and 8-hexadecene, 1,4-difluoro-2-butylene, 1,2-ditrifluoromethyl ethylene, 3-chloro-1-propylene, 4-chloro-1-butylene, 3-chloro-2-butylene, 1,4-dichloro-2-butene, 1,1,4,4-tetrachloro-2-butene, 6-chloro-1-hexene, 1,6-dichloro-3-hexene, 7-chloro-1-heptene, 7,6-dichloro-2-heptene, 1,7-chloro-3-heptene, 3,5,7-trichloro-1-octene, 1,8-dichloro-4-octene, 1,2-dicyclobutyl ethylene, 1,2-dicyclohexyl ethylene, 1,2-dicyclopentyl ethylene, 1,2-dicyclododecyl ethylene, 3-hydroxy-1-propene, 1,6-dihydroxy-3-hexene, 3-methoxy-1-propene, 1,4-dimethoxy-1-butene, 1,6-dimethoxy-3-hexene, 1,6-dipropoxy-3-hexene, 1,10-dimethoxy-5-decene, 1,10-dicarbohexoxy-5-decene, 1,4-dicarbomethoxy-2-butene, 1,8-dicarbomethoxy-4-octene, 1,8-dicarboethoxy-4-octene, 1,8-dicarbomethoxy-2,7-dicyclohexyl-4-octene, 1,4-dicyano-2-butene, 1,6-dicyano-3-hexene, 1-cyano-3-pentene, 2-cyano-3-pentene, phenylethylene, 1,2-diphenylethylene, 1,4-diphenyl-2-butene, 1,2-di-(p-chlorophenyl)-ethylene, 1,2-di-(p-methoxyphenyl)-ethylene, 1,2-di-(p-fluorophenyl)-ethylene, 1,2-di-(2,4-dimethylphenyl)-ethylene, 1,2-di-(p-cyclohexylphenyl)-ethylene, 1,2-di-(2-chloro-4-tert.-butylphenyl)-ethylene, 1,2-di-(1-tert.-butylphenyl)-ethylene, 1,4-divinylbenzene, 2,4-divinylbenzene, p-chlorophenylethylene and p-fluorophenylethylene.

One preferred group of olefins corresponds to the general formula (II):

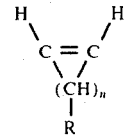

in which n is an integer from 3 to 5 and each of the C-atoms defined by n can be substituted by R independently of one another where R represents fluorine, chlorine, cyanide, $C_1$-$C_6$-alkoxy, $C_1$-$C_6$alkyl, $C_5$-$C_7$-cycloalkyl or a phenyl group optionally substituted by fluorine, chlorine, cyanide, $C_1$-$C_6$-alkoxy.

The following are mentioned by way of example: Cyclopentene, 3-chloro-1,2-cyclopentene, 3,5-dichloro-1,2-cyclopentene, 4-hydroxy-1,2-cyclopentene, 3,5-dimethyl-1,2-cyclopentene, 3,5-diethyl-1,2-cyclopentene, 4-isopropyl-1,2-cyclopentene, 4-tert.-butyl-1,2-cyclopentene, 3,5-diphenyl-1,2-cyclopentene, 3,5-di-(4-chlorophenyl)-1,2-cyclopentene, 4-phenyl-1,2-cyclopentene, 3-methoxy-1,2-cyclopentene, 4-propoxy-1,2-cyclopentene, 3,5-diisopropoxy-1,2-cyclopentene, 4-tert.-butoxy-1,2-cyclopentene, 4-n-hexoxy-1,2-cyclopentene, 3-carbomethoxy-1,2-cyclopentene, 4-carbopropoxy-1,2-cyclopentene, 3,5-di[($\beta$-carbomethoxy)-ethyl]-1,2-cyclopentene, 3-cyano-1,2-cyclopentene, 4-cyanocyclopentene, 4-($\beta$-cyanoethyl)-1,2-cyclopentene, 3-fluoro-1,2-cyclopentene, 3-trifluoromethyl-1,2-cyclopentene, cyclohexene, 3-fluoro-1,2-cyclohexene, 3-trifluoromethyl-1,2-cyclohexene, 3-chloro-1,2-cyclohexene, 4-chloro-1,2-cyclohexene, 5-chloro-1,2-cyclohexene, 4,5-dichloro-1,2-cyclohexene, 3-hydroxy-1,2-cyclohexene, 3,5-dihydroxy-1,2-cyclohexene, 3-methyl-1,2-cyclohexene, 4-methyl-1,2-cyclohexene, 5-ethyl-1,2-cyclohexene, 3,5-diisopropyl-1,2-cyclohexene, 4,5-di-n-hexyl-1,2-cyclohexene, 4-phenyl-1,2-cyclohexene, 4,5-diphenyl-1,2-cyclohexene, 4-(p-chlorophenyl)-1,2-cyclohexene, 3-methoxy-1,2-cyclohexene, 4-ethoxy-1,2-cyclohexene, 5-isopropoxy-1,2-cyclohexene, 4-hexoxy-1,2-cyclohexene, 4-($\beta$-cyanoethyl)-1,2-cyclohexene, cycloheptene, 3-methyl-1,2-cycloheptene, 3,7-dimethyl-1,2-cycloheptene, 4,5,6-trimethyl-1,2-cycloheptene, 5-isopropyl-1,2-cycloheptene, 5-tert.-butyl-1,2-cycloheptene, 3-chlorocycloheptene, 4-($\beta$-chloroethyl)-1,2-cycloheptene, 4,6-dichloro-1,2-cycloheptene, 5-hydroxy-1,2-cycloheptene, 4,5-dihydroxy-1,2-cycloheptene, 3-phenyl-1,2-cycloheptene, 5-phenyl-1,2-cycloheptene, 4,6-di-[(p-tert.-butyl)-phenyl]-1,2-cycloheptene, 3-methoxy-1,2-cycloheptene, 5-methoxy-1,2-cycloheptene, 3-propoxy-1,2-cycloheptene, 5-tert.-butoxy-1,2-cycloheptene, 3-carbomethoxy-1,2-cycloheptene, 4-carbomethoxy-1,2-cycloheptene, 3,7-dicarbomethoxy-1,2-cycloheptene and 5-($\beta$-carbomethoxy)-ethyl-1,2-cycloheptene.

The quantities in which the compound of boron and the compound of a metal of the 5th and/or 6th Secondary Group are used can fluctuate within wide limits. In general, only small quantities will be added; this applies in particular to the quantities of compounds of metals of the 5th and/or 6th Secondary Group used.

Thus, the quantity in which the compounds of metals of the 5th and/or 6th Secondary Group is added is generally less than 10 mol percent of the quantity of hydrogen peroxide used, quantities of from 0.01 to 1 mol percent, based on the quantity of hydrogen peroxide, being preferred.

The quantity in which the boron compound is added can also vary within wide limits. However, it is generally larger than the quantity in which the compounds of metals of the 5th and/or 6th Secondary Group is used. In general, the boron compound is generally used in quantities of from 10 to 50 mol percent, based on the quantity of hydrogen peroxide used, quantities of from 20 to 30% being preferred.

The compounds added can be either soluble and insoluble in the reaction mixture. It is advantageous to apply the compounds to inert supports, for example aluminium oxide, aluminium oxide hydrate, silica gel or zeolites, and to use them in this form.

Suitable compounds of boron include boron oxides, boric acids, salts and esters of boric acids, boron-halogen compounds, boron phosphates and complex boron compounds.

The following are mentioned as examples of boric acids: orthoboric acid, metaboric acid and tetraboric acid. Suitable salts include the alkali and alkaline earth salts of these acids, also their zinc and aluminium salts. The following salts are mentioned by way of example:

Sodium orthoborate, sodium metaborate, sodium tetraborate, lithium orthoborate, lithium metaborate, lithium tetraborate, potassium orthoborate, potassium metaborate, potassium tetraborate, magnesium orthoborate, magnesium tetraborate, magnesium metaborate, calcium orthoborate, calcium metaborate, calcium tetraborate, zinc orthoborate, zinc metaborate, zinc tetraborate, aluminium orthoborate, aluminium metaborate and aluminium tetraborate.

Suitable boric acid esters are compounds corresponding to the general formula (III)

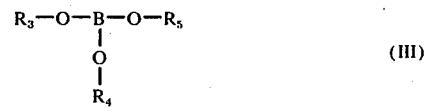

in which $R_3$, $R_4$ and $R_5$ independently of one another represent a $C_1$-$C_6$-alkyl group optionally substituted by hydroxyl, fluorine, chlorine, $C_1$-$C_3$-alkoxy or phenyl, a $C_5$-$C_7$-cycloalkyl group or a phenyl group optionally substituted by fluorine, chlorine or $C_1$-$C_3$-alkyl. The following are mentioned as examples of $R_3$, $R_4$ and $R_5$: Chloromethyl, hydroxymethyl, $\beta$-hydroxymethyl, $\beta$-methoxyethyl, 3-propoxypropyl, toluene, ethylphenyl, propylphenyl and tert.-butylphenyl.

The following are mentioned as examples of boric acid esters:

Boric acid trimethyl ester, boric acid triethyl ester, boric acid tri-n-hexyl ester, boric acid tricyclohexyl ester, boric acid tri-($\beta$-methoxyethyl)-ester, boric acid tri-($\beta$-fluoroethyl)-ester, boric acid triphenylester, boric acid tri-(p-chlorophenyl)-ester, boric acid tri-(p-methoxyphenyl)-ester and boric acid tri-($\beta$-hydroxyethyl)-ester.

Boron trifluoride and boron trichloride are mentioned as representatives of halogen compounds of boron. Suitable complex boron compounds are compounds which represent adducts of alcohols of the general formula $R_3$—OH, of alcoholates of the general formula $R_3$—OMe, of ethers corresponding to the general formula $R_3$—O—$R_4$, of carboxylic acids corresponding to the general formula $R_3$—COOH or of hydrogen halide, with compounds of general formula III, boron trifluoride or boron trichloride, $R_3$ and $R_4$ having the same meaning as in general formula III whilst Me in the case of the alcoholates can represent the alkali and alkaline-earth metals, also zinc and aluminium. The following are mentioned as examples of complex boron compounds:

Tetramethoxy boric acid, lithium tetramethoxy borate, sodium tetramethoxy borate, magnesium ditetramethoxy borate, zinc ditetramethoxy borate, boron trifluoride diethyl etherate, boron trifluoride trimethyl etherate, boron trifluoride acetic acid, boron trifluoride propionic acid, tetrafluorboric acid and sodium trimethoxy monocyclohexyloxy borate.

Boric acid anhydride can also be added.

Suitable compounds of the metals of the 5th and/or 6th Secondary Group include in particular compounds of the metals vanadium, niobium, chromium, molybdenum and tungsten, compounds of molybdenum and vanadium being preferred. It is also preferred to use salts of these elements with organic acids, for example acetates, benzoates, naphthenates or acetyl acetonates. The following are mentioned by way of example:

Vanadium-(II)-acetate, vanadium-(II)-acetylacetonate, vanadium-(II)-benzoate, vanadium-(II)-naphthenate, vanadium-(III)- acetate, vanadium-(III)-acetylacetonate, vanadium-(III)-benzoate, vanadium-(III)-naphthenate, vanadyl acetylacetonate, vanadyl naphthenate, niobium acetate, chromium-(II)-acetate, chromium-(II)-acetylacetonate, chromium-(III)-acetate, chromium-(III)-acetyl acetonate, chromium-(III)-naphthenate, molybdenum-(II)-acetyl acetonate, molybdenum-(II)-acetate, molybdenum-(II)-benzoate, molybdenum-(III)-acetylacetonate, molybdenum-(III)-acetate, molybdenum-(III)-benzoate, molybdenum naphthenates, molybdenum acetyl acetonates, tungsten-(III)-acetate and tungstyl acetyl acetonate.

It is also possible to add to the reaction mixture complex compounds of the elements of the 5th and 6th Secondary Group such as, for example, carbonyl, nitrosocarbonyls or carbonylates. Molybdenum hexacarbonyl and chromium hexacarbonyl are mentioned as examples.

In one preferred embodiment of the process according to the invention, compounds of the alkali metals are added in addition to the compound of boron and the compound of a metal of the 5th and 6th Secondary Group, which increases the selectivity of the reaction, based on the hydrogen peroxide used. Compounds such as these are the acetates, bicarbonates, carbonates and alcoholates of the alkali metals. In addition, it is possible instead of adding the compounds of the alkali metals to add tertiary esters such as triethylamine for example.

In general, the process according to the invention is carried out by initially introducing into the reactor hydrogen peroxide together with the boron compound and the compound of a metal of the 5th and/or 6th Secondary Group and adding the olefin, or alternatively by initially introducing the olefin together with the boron compound and the compound of a metal of the 5th and/or 6th Secondary Group and adding the hydrogen peroxide.

In one preferred procedure, hydrogen peroxide is used in the form of a non-aqueous solution. Non-aqueous hydrogen peroxide solutions of this kind are obtained as known per se, for example in accordance with DAS No. 1,802,003. In general, these non-aqueous solutions are prepared by adding a solvent miscible with water and hydrogen peroxide to an aqueous hydrogen peroxide solution and subsequently removing the water, preferably by distillation in vacuo. Solvents suitable for this purpose are in particular esters, N-alkyl-substituted acid amides, alcohols, carboxylic acids, sulphonic acids and phosphoric acids. The esters and alkylamides of the phosphoric acids, phosphonic acids and phosphinic acids are particularly suitable, the following being mentioned by way of example: triethyl phosphate, methane phosphonic acid dimethyl ester, β-cyanoethylphosphonic acid dimethyl ester, β-carbomethoxyphosphonic acid methyl ester, trioctyl phosphate, trihexyl phosphate, butyl acetate, isoamyl acetate and cyclo hexyl acetate.

It is also advantageous to use solvent mixtures which afford advantages over the use of a single solvent in regard to their dissolving properties for the simultaneous dissolution of hydrogen peroxide, the added boron compound and the added compound of a metal of the 5th and/or 6th Secondary Group, olefin and the aldehydes formed. These advantages are reflected in the fact that it is possible to start with a more highly concentrated parent solution of hydrogen peroxide in a phosphonic acid ester or phosphoric acid ester, for example a 30% solution of hydrogen peroxide in methane phosphonic acid dimethyl ester, to add to the solution an inert solvent for example ethyl acetate, butyl acetate or methylene chloride, thereby increasing the solubility of the added boron compound and of the added compound of a metal of the 5th and 6th Secondary Group and of the olefin used.

In another preferred procedure, hydrogen peroxide is used in a solvent immiscible or substantially immiscible with water, for example butyl acetate or trioctyl phosphate, and the reaction products removed on completion of the reaction by extraction with water, leaving aqueous solutions of the reaction products which are either directly further processed or from which the individual reaction products are isolated in conventional manner.

The concentration of the non-aqueous hydrogen peroxide solutions used can fluctuate within wide limits and in practice this is determined solely by the explosion limits. Accordingly, the upper limit to the hydrogen peroxide concentration will generally be from 30 to 60%, depending upon the solvent used. In general, the hydrogen peroxide is used in a concentration of from 3 to 30%, the use of non-aqueous solutions of hydrogen peroxide with a concentration of from 10 to 20% being preferred.

The molar ratio of olefin to hydrogen peroxide in the starting solution can vary within wide limits. However, it is advantageous, if the hydrogen peroxide used is to be completely reacted, to use an excess of olefin of generally from 10 to 500 mol percent and preferably from 15 to 100 mol percent.

The temperature at which the process according to the invention is carried out is essentially governed by the stability of the hydrogen peroxide in the corresponding reaction mixture, the solvent used and the added compounds of boron and of a metal of the 5th and/or 6th Secondary Group playing an important part. Accordingly, the process is carried out at temperatures in the range from −80° to +50°C, depending upon the type and concentration of the solvent used.

The pressure is determined by the vapour pressure of the reactants and of the solvent in the starting solution and does not critically affect the reaction in any way. The process according to the invention can be carried out both in the gaseous phase and in the liquid phase.

The reaction time differs according to the olefin used, the reaction temperature and the added compounds of boron and of a metal of the 5th and/or 6th Secondary Group. However, it is generally very short. Thus, the reaction is generally substantially complete, after the reactants have been mixed and can be completed simply by stirring the reaction mixture.

In some cases, the aldehyde does not immediately exist completely as such. In such cases, it is best to reheat the the reaction mixture to an elevated temperature, for example to around 80° to 100°C, on completion of the reaction. The addition of acids, for example sulphuric acid, hydrochloric acid or hydrofluoric acid, has an accelerating effect here.

The aldehydes are isolated by methods known per se, for example by distillation. In one particularly preferred embodiment of the process according to the invention, the reaction is carried out in a water-immiscible solvent for example, trioctyl phosphate, tributyl phosphate, isoamyl acetate, butyl acetate or cyclohexyl acetate, and the aldehydes obtained isolated by extraction with water from the reaction mixture, optionally at boiling temperature.

EXAMPLE 1

7.05 g of cyclopentene were added dropwise with stirring to a mixture heated to 30°C of 52.1 g of a 4.8% solution of hydrogen peroxide in isoamyl acetate, 0.207 g of molybdenum-(III)-acetyl acetonate and 0.864 g of boric acid anhydride.

After 30 minutes, the mixture contained 5.43% of glutardialdehyde according to analysis by gas chromatography in a 2m column with 5% of nitrile silicone on silanised acid-washed kieselguhr with cyclohexyl acetate as internal standard.

The reaction mixture was poured into boiling water. After phase separation, a lower aqueous phase containing 2.8 g of glutardialdehyde was obtained, the upper phase containing 0.4 g of glutardialdehyde.

The glutardialdehyde content of the aqueous solution was determined as known per se by reaction with hydroxylammonium hydrochloride and by titration of the hydrochloric acid liberated.

If the test is carried out in the absence of boric acid anhydride, the mixture contains 1.6% of glutardialdehyde after 30 minutes and 1.94% of glutardialdehyde after 3 hours.

EXAMPLE 2

20.4 g of cyclopentene were added with stirring to a mixture heated to 30°C of 54.3 g of a 9.2% solution of hydrogen peroxide in triisooctyl phosphate, 4.0 g of boric acid anhydride and 0.6 g of molybdenum-(III)-acetyl acetonate. After 3 hours, the mixture had the following composition according to analysis by gas chromatography:

| | |
|---|---|
| Glutardialdehyde: | 7.12% |
| Cyclopentene oxide: | 0.71% |
| Cyclo-1,2-pentane diol: | less than 0.1% |

The insoluble constituents were centrifuged off and the residual heavy-metal ions removed with aluminium oxide. The mixture was then poured into boiling water and phase separation awaited. An aqueous solution containing 5.6 of glutardialdehyde was obtained in this way.

EXAMPLE 3
(comparison Example to Example 2)

20.4 g of cyclopentene were added dropwise with stirring to a mixture heated to 30°C of 47.0 g of a 10.65% hydrogen peroxide solution in triisooctyl phosphate and 0.6 g of molybdenum-(III)-acetylacetonate.

After 4 hours, the reaction mixture had a glutardialdehyde content of 3.08% according to analysis by gas chromatography.

EXAMPLE 4

20.4 g of cyclopentene were added dropwise at 30°C to a stirred mixture of 49.0 g of a 10.2% solution of hydrogen peroxide in triisooctylphosphate, 0.6 g of molybdenum-(III)-acetyl acetonate and 2.5 g of boric acid anhydride. After 3 hours, analysis of the reaction mixture by gas chromatography produced the following results:

| | |
|---|---|
| Glutardialdehyde: | 7.58% |
| Cyclopentene oxide: | 1.18% |
| Cyclo-1,2-pentane diol | 0.1% |

EXAMPLE 5

20.4 g of cyclopentene were added dropwise at 30°C to a mixture of 33.9 g of a 14.74% solution of hydrogen peroxide in tributyl phosphate, 0.6 g of molybdenum-(III)-acetyl acetonate and 2.5 g of boric acid anhydride. After 4 hours, the reaction mixture was acidified to pH 1 with 2N sulphuric acid and heated for 10 minutes to 100°C. After cooling to room temperature, analysis of the reaction mixture by gas chromatography showed that it contained 6.3 g of glutardialdehyde.

EXAMPLE 6

24.6 g of cyclohexene were added dropwise to a mixture heated to 30°C of 49.0 g of a 10.2% solution of hydrogen peroxide in triisooctylphosphate, 0.6 g of molybdenum-(III)-acetyl acetonate and 2.5 g of boric acid anhydride. After 3 hours, analysis of the reaction mixture by gas chromatography showed that it contained 4.3% of adipine aldehyd.

EXAMPLE 7

20.4 g of cyclopentene were added dropwise with stirring at 30°C to 43.4 g of an 11.53% solution of hydrogen peroxide in triisooctylphosphate, 0.6 g of molybdenum-(III)-acetyl acetonate and 2.5 g of boric acid trimethyl ester.

After 4 hours, analysis of the reaction mixture by gas chromatography showed that it contains 6.5% of glutardialdehyde and 0.5% of cyclopentene oxide.

EXAMPLE 8

31.2 g of freshly distilled styrene were added dropwise with stirring to 43.4 g of an 11.53% solution of hydrogen peroxide in triisooctylphosphate, 0.6 g of molybdenum-(III)-acetyl acetonate and 2.5 g of boric acid anhydride.

After 2 hours, the reaction mixture was found by gas-chromatographic analysis to contain 5.2% of benzaldehyde and 1.8% of formaldehyde.

What is claimed is:

1. Process for preparing aldehydes which comprises reacting an olefin having the formula (I);

wherein $R_1$ and $R_2$ independently of one another are selected from the group of hydrogen; phenyl optionally substituted by fluorine, $C_1$-$C_6$ alkoxy or $C_1$-$C_6$ alkyl;

linear or branched $C_1$-$C_{12}$-alkyl optionally substituted by fluorine, —OH, $C_1$-$C_6$ alkoxy, carbo- $C_1$-$C_3$ -alkoxy or phenyl; or the radicals $R_1$ and $R_2$ together with the C-atoms of the C=C-double bond can represent a carbocyclic ring with up to 24 carbon atoms optionally substituted by fluorine, $C_1$-$C_6$-alkyl, $C_5$-$C_7$ -cycloalkyl or phenyl, with a non-aqueous solution of hydrogen peroxide in a solvent selected from the group of esters, N-alkyl-substituted acid amides, alcohols, carboxylic acids, sulfonic acids and phosphoric acids, at temperatures in the range of from −80°C to +50°C in the presence of a boron compound selected from the group of a boron oxide, a boric acid and a boric acid ester having the formula

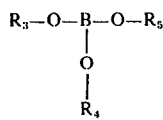

wherein $R_3$, $R_4$ and $R_5$ independently of one another represent $C_1$-$C_6$-alkyl, $C_5$-$C_7$-cycloalkyl, or phenyl, and at least one vanadium (II) or (III) or molybdenum (II) or (III) acetate, benzoate, acetyl acetonate or naphthenate, said boron compound being present in quantities of from 10 to 50 mol percent based on the quantity of hydrogen peroxide used and said vanadium or molybdenum compound being present in quantities of less than 10 mol present based on the quantity of hydrogen peroxide used.

2. Process of claim 1 wherein the olefin has the formula (II):

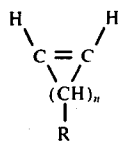

wherein $n$ is an integer from 3 to 5 and each of the C-atoms defined by $n$ can be substituted by R independently of one another where R is selected from the group of fluorine, $C_1$-$C_6$-alkoxy, $C_1$-$C_6$-alkyl, $C_5$-$C_7$-cycloalkyl and a phenyl group optionally substituted by fluorine, or $C_1$-$C_6$-alkoxy.

3. Process of claim 1 wherein the olefin is selected from the group of cyclohexene and styrene.

4. Process of claim 1 wherein the boron compound is boric acid trimethyl ester.

5. Process of claim 1 wherein molybdenum-(III)-acetyl acetonate is used.

6. Process of claim 1 carried out in the presence of a mixture of boric acid anhydride and molybdenum-(III)-acetyl acetonate.

7. Process of claim 1 carried out in the presence of a mixture of boric acid trimethyl ester and molybdenum-(III)-acetyl acetonate.

8. Process of claim 1 wherein the solvent is selected from the group of an alcohol, carboxylic acid ester, N-alkyl-substituted acid amides as the solvent for hydrogen peroxide.

9. Process of claim 1 wherein an ester of an alkylamide of a phosphoric acid, phosphonic acid or phosphinic acid is used as the solvent for hydrogen peroxide.

10. Process of claim 1 wherein a non-aqueous solution of hydrogen peroxide in tributyl phosphate, trioctyl phosphate or isoamylacetate is used.

11. Process of claim 1 wherein the vanadium or molybdenum compound is added in a quantity of from 0.01 to 1 mol percent, based on the hydrogen peroxide.

12. Process of claim 1 wherein the boron compound is added in a quantity of from 20 to 30 mol percent based on the hydrogen peroxide.

* * * * *